(12) United States Patent
Webb (10) Patent No.: US 7,174,781 B2
(45) Date of Patent: Feb. 13, 2007

(54) TEMPERATURE REDUCTION FIXTURE FOR ACCELERATED WEATHERING TEST APPARATUS

(75) Inventor: David Robert Webb, Surprise, AZ (US)

(73) Assignee: Atlas Material Testing Technology, L.L.C., Chicago, IL (US)

( * ) Notice: Subject to any disclaimer, the term of this patent is extended or adjusted under 35 U.S.C. 154(b) by 47 days.

(21) Appl. No.: 11/047,236

(22) Filed: Jan. 31, 2005

(65) Prior Publication Data

US 2006/0169037 A1  Aug. 3, 2006

(51) Int. Cl.
*G01W 1/00* (2006.01)

(52) U.S. Cl. .................. 73/170.16; 73/170.27

(58) Field of Classification Search .............. 73/170.16
See application file for complete search history.

(56) References Cited

U.S. PATENT DOCUMENTS

| | | | |
|---|---|---|---|
| 4,500,642 A * | 2/1985 | Reiji et al. .................... 501/54 |
| 4,807,247 A * | 2/1989 | Robbins, III .................. 374/57 |
| 4,817,447 A * | 4/1989 | Kashima et al. ........... 73/865.6 |
| 4,874,952 A | 10/1989 | Arnaud et al. |
| 5,138,892 A | 8/1992 | Suga |
| 6,073,500 A | 6/2000 | Jorgensen et al. |
| 6,533,452 B1 | 3/2003 | Hardcastle, III |
| 6,604,436 B1 * | 8/2003 | Lewandowski et al. .... 73/865.6 |
| 6,659,638 B1 | 12/2003 | Hardcastle, III |
| 6,892,591 B2 * | 5/2005 | Grossman et al. ......... 73/865.6 |
| 6,990,868 B2 * | 1/2006 | Hardcastle, III ........... 73/865.6 |
| 2001/0038269 A1 | 11/2001 | Grossman et al. |
| 2003/0133184 A1 | 7/2003 | Fischer, Jr. et al. |
| 2003/0214996 A1 | 11/2003 | Hardcastle, III |

* cited by examiner

*Primary Examiner*—Max Noori
(74) *Attorney, Agent, or Firm*—Vedder Price Kaufman & Kammholz (57) ABSTRACT

An accelerated weathering test apparatus of the type used to concentrate solar radiation upon test specimens including a fixture connected to a target board including a frame spaced from the target board a predetermined distance by a plurality of stand-offs and having at least one opening defined therein and a transparent element connected to the frame in alignment with each at least one opening in a covering orientation such that the solar radiation from a reflecting solar concentrator impinges upon the test specimens. The predetermined distance is configured such that the frame functions as an extension of a deflector and an operating temperature of the test specimens is shielded from external influences.

31 Claims, 5 Drawing Sheets

TEMPERATURE REDUCTION FIXTURE FOR ACCELERATED WEATHERING TEST APPARATUS

BACKGROUND

The present disclosure is directed to an accelerated weathering test apparatus of the type used to concentrate solar radiation on test specimens, and more particularly, to an accelerated weathering test apparatus with a fixture that facilitates a reduction in the operating temperature of the test specimens.

Manufacturers of exterior coatings, such as paints and finishes, as well as plastics and other components which tend to degrade under exposure to solar radiation and other weathering effects, often want to know how such products will perform following years of exposure. However, such manufacturers typically require such information in a much shorter time than it would take to expose such materials to weathering effects under normal conditions. Accordingly, accelerated weathering test devices have been developed which accelerate the effects of weathering due to outdoor exposure in a much shorter time so that manufacturers need not actually wait five or ten years in order to determine how their products will hold up after five or ten years of actual outdoor exposure.

One known accelerated weathering test device is disclosed in U.S. Pat. No. 2,945,417, issued to Caryl et al. The aforementioned test device includes a Fresnel-reflecting solar concentrator having a series of ten flat mirrors which focus natural sunlight onto a series of test specimens secured to a target board measuring approximately five (5) inches wide by fifty-five (55) inches long. The Fresnel-reflecting solar concentrator directs solar radiation onto the target board area with an intensity of approximately eight suns. Both the bed which supports the mirrors of the solar concentrator, and the target board, are supported by a frame which can be rotated to follow daily movements of the sun.

A solar tracking mechanism responsive to the position of the sun, controls the operation of an electric motor that is used to rotate the test apparatus to follow movements of the sun. The axis of rotation of the test machine is oriented in a north-south direction, with the north elevation having altitude adjustment capability to account for variation in the sun's altitude at various times during the year.

Such known testing devices are also provided with an air tunnel mounted above the target board. An air deflector causes air escaping from the air tunnel to be circulated across the test specimens mounted to the target board to prevent the test specimens from overheating due to the concentrated solar radiation to which they are exposed. The amount of air is controlled by the dimension of the gap between the deflector and the specimen. A squirrel cage blower communicates with the air tunnel for blowing cooling ambient air there through. In addition, water spray nozzles are provided proximate to target board for wetting the test samples at periodic intervals to simulate the weathering effects of humidity, dew, rain, etc.

Another known accelerated weathering test device is disclosed in U.S. Pat. No. 4,807,247. issued to Robins. The aforementioned test device includes all the structure previously described above with respect to the '417 patent and further includes a system for maintaining a uniform, constant test specimen temperature during daylight hours despite variations in ambient air temperature and variations in solar radiation intensity.

The system includes a temperature sensor mounted to the target board for exposure to the concentrated solar radiation and for generating an electrical signal indicative of the temperature of the test specimen mounted to the target board. The system further includes a control mechanism electrically coupled to the temperature sensor and responsive to the electrical signal generated thereby for selectively controlling the application of electrical power to the electrical motor included within the air circulation system. In this manner, the control mechanism serves to vary the speed of the electric motor and thereby control the flow rate of cooling ambient air circulating across the target board so that the temperature of the test specimen remains constant at the desired set point.

When the sensed temperature of the test specimen increases, the control mechanism increases the speed of the blower motor to circulate more cooling ambient air across the target board in order to lower the temperature of the test samples back to the desired set point. Similarly, if the sensed temperature of the target samples drops below the desired nominal temperature, the control mechanism decreases the speed of the blower to permit the test samples to warm up back to the desired set point.

The temperature control mechanism also includes a user operable adjustment mechanism, in the form of the control knob, for allowing a user to set a static, desired target specimen temperature. A bypass switch is also provided for allowing the user to operate the test device in the controlled temperature-mode as described above, or in an uncontrolled mode wherein the blower motor operates at a constant speed.

Standardized testing methods have been developed for operating accelerated weathering test devices of the type described above. The American Society for Testing and Materials (ASTM) has issued standards G90, E838, D4141, D3105, D3841, D5105, E1596 and D4364 covering the testing procedures and the operating parameters for conducting such outdoor accelerated weathering tests. Other standards and appraisals have also been developed and specified by the Society of Automotive Engineers (SAE), Ford, International Standards Organization (ISO), American National Standards Institute (ANSI), Japan Industrial Standard (JIS), namely, SAE J576, SAE J1961, Ford EJB-M1J14-A, Ford EST-M5P11-A, ISO 877, ANSI/NSF 54, JIS Z 2381 and MIL-T-22085D.

Apart from outdoor accelerated weathering test devices of the type described above, other test devices are also known which utilize an artificial source of radiation to expose the test specimens. An example of such a test device is disclosed in U.S. Pat. No. 3,664,188 issued to Kockott. While such test devices have the advantage of permitting precise control over radiation intensity, temperature and humidity, such test devices have often failed to duplicate the actual light spectrum of natural sunlight to which the specimens under test will actually be exposed in everyday use. It has been acknowledged and recognized by those of skill in the art that natural sunlight and artificial sunlight test apparatus are distinct from one another and provide different sets of empirical data.

Outdoor accelerated weathering test devices of the type described above in regard to U.S. Pat. Nos. 2,945,417 and 4,807,247, have the advantage of using natural sunlight, and hence the specimens under test are exposed to the actual spectrum of sunlight. However, disadvantages of outdoor accelerated weathering test devices have been discovered.

One such disadvantage is that the temperature of test specimens cannot be precisely controlled due to exposure to outdoor conditions. For example, exposure to multiples of incident sunlight can raise the temperature of a specimen beyond an acceptable testing range. Furthermore, the temperature of the specimen may rise high enough to damage the test specimen. To solve this problem, accelerated weathering test devices have been devised that attempt to cool the test specimen by artificially blowing air over the test specimen. However, when the outside conditions are windy, the disturbance from the wind degrades the cooling effects of the artificially blown air over the test specimen.

Therefore, there exists a need in the art for a device and a method of controlling the temperature and temperature fluctuations of a test specimen in an outdoor accelerated weathering test apparatus regardless of ambient wind disturbances.

SUMMARY

In accordance with one principle aspect to the present disclosure, an accelerated weathering test apparatus of the type used to concentrate solar radiation upon test specimens including a fixture connected to a target board including a frame spaced from the target board a predetermined distance by a plurality of stand-offs and having at least one opening defined therein and a transparent element connected to the frame in alignment with each at least one opening in a covering orientation such that the solar radiation from a reflecting solar concentrator impinges upon the test specimens. The predetermined distance is configured such that the frame functions as an extension of a deflector and an operating temperature of the test specimens is shielded from external influences.

In another principle aspect of the present disclosure, a fixture is adapted for use in connection with an accelerated weathering test apparatus of the type used to concentrate solar radiation upon test specimens. The fixture includes a frame having at least one opening and a transparent element connected to the frame in alignment with each at least one opening in a covering orientation such that the solar radiation from the reflecting solar concentrated impinges upon the test specimens. A plurality of stand-offs are operatively contiguous with the frame and target board to space the frame from the target board a predetermined distance such that the frame functions as an extension of the deflector and an operating temperature of the test specimens is shielded from external influences.

In another principle aspect of the present disclosure, an accelerated weathering test apparatus of the type used to concentrate solar radiation upon test specimens includes a fixture connected to a target board including a substantially planar frame spaced from the target board a predetermined distance by a plurality of stand-offs. The frame also has a plurality of openings that are in registration with the test specimens and a plurality of transparent elements formed from an ultraviolet transmissive material connected to the frame, each transparent element in alignment with one of the openings such that the solar radiation from the reflecting solar concentrator impinges upon the test specimens. The predetermined distance is configured such that the frame functions as an extension of the deflector so that the air circulated across the test specimens is compressed between the frame and target board to facilitate increased heat transfer from the test specimens and an operating temperature of the test specimens is maintained in a narrow range close to a desired test specimen temperature, shielded from external influences.

In another principle aspect of the present disclosure, an accelerated weathering test apparatus of the type used to concentrate solar radiation upon test specimens at a first temperature includes a fixture connected to the target board including a frame spaced from the target board a predetermined distance by a plurality of stand-offs. The frame also has at least one opening defined therein, and a transparent element connected to the frame in alignment with each at least one opening in a covering orientation such that the solar radiation from the reflecting solar concentrator impinges upon the test specimens. The predetermined distance is configured such that the frame functions as an extension of the deflector and an operating temperature of the test specimens is less than the first temperature and is shielded from external influences.

BRIEF DESCRIPTION OF THE DRAWINGS

Certain embodiments are shown in the drawings. However, it is understood that the present disclosure is not limited to the arrangements and instrumentality shown in the attached drawings, wherein.

DETAILED DESCRIPTION

For the purposes of promoting and understanding the principles disclosed herein, reference will now be made to the preferred embodiments illustrated in the drawings and specific language will be used to describe the same. It will nevertheless be understood that no limitation of the scope is thereby intended. Such alterations and further modifications in the illustrated device and such further applications are the principles disclosed as illustrated therein as being contemplated as would normally occur to one skilled in the art to which this disclosure relates.

Figure 1:
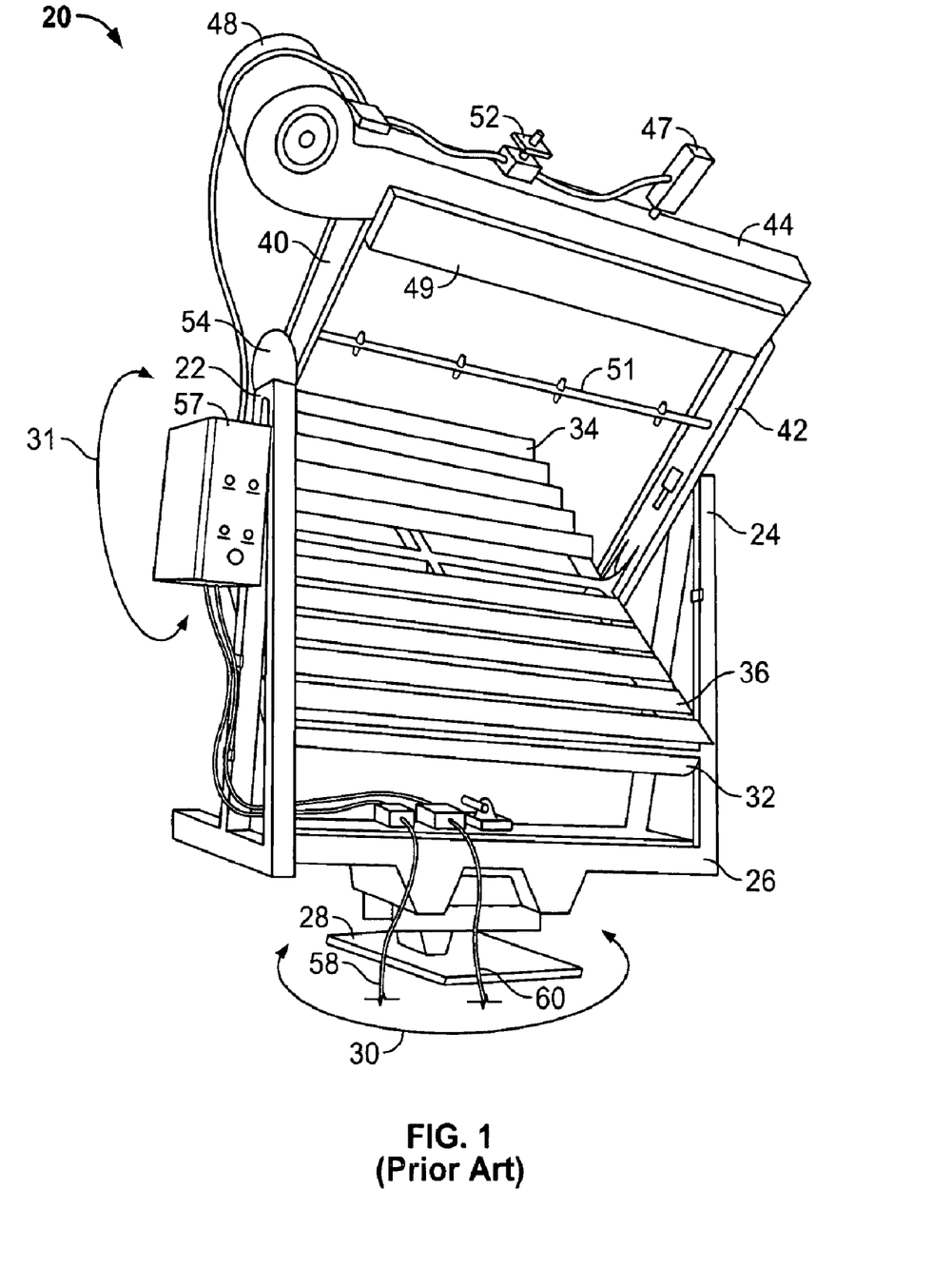
FIG. 1 illustrates a perspective view of an accelerated weathering test apparatus.

Referring to FIG. 1, a prior art accelerated weathering test apparatus is designated generally by reference 20 and includes a pair of A-frame members 22 and 24 to support the operative portion of the apparatus. The lower ends of the A-frame members 22, 24 are interconnected by a base member 26 which is operatively connected to a ground member 28 in order to provide azimuth rotation in the direction indicated by arrow 30 and elevation rotation in the direction indicated by arrow 31. The elevation direction rotation accounts for periodic variation in the sun's altitude at solar noon.

Rotatively supported from the upper ends of A-frame members 22, 24 is a mirror bed frame 32 which supports a plurality of flat mirrors, including those designated by reference numerals 34 and 36. The plurality of mirrors 34, 36 are angled to reflect solar radiation directly impinging upon such mirrors to a target board 38 (see FIG. 2).

Figure 2:
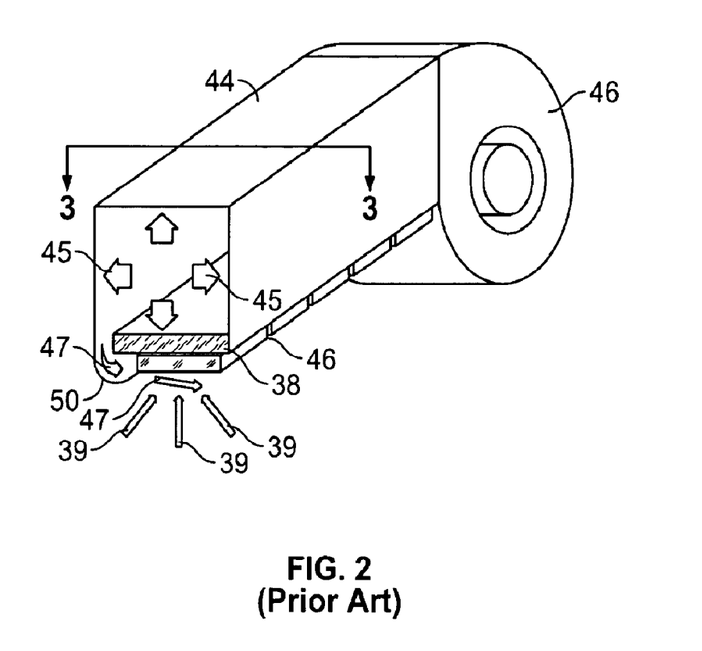
FIG. 2 illustrates a perspective sectional view of an air tunnel of the accelerated weathering test apparatus of FIG. 1.
Figure 3:
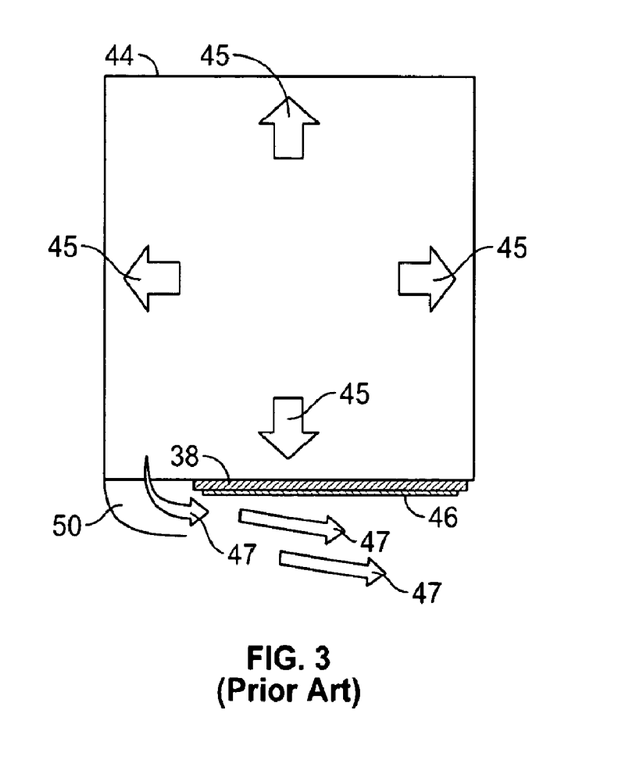
FIG. 3 illustrates a cross sectional view of the air tunnel of FIG. 2.

A pair of standards 40 and 42 extend outwardly from and perpendicular to mirror bed frame 32. An air tunnel 44 having a generally rectangular cross section is supported by the upper ends of standards 40, 42. Referring to FIGS. 2 and 3, target board 38 is supported by the lower wall of air tunnel 44, and a plurality of test specimens 46 are mounted to the target board 38 for exposure to the concentrated solar radiation, represented in FIG. 2 by the upwardly extending arrows numbered 39. The target board 38 may include a single specimen 46 or a plurality of similar or different test specimens 46, which may be referred to herein as test specimen(s) 46.

A squirrel cage blower assembly 48 communicates with one end of the air tunnel 44. Squirrel cage blower assembly 48 includes a fan driven by an electric motor to circulate cooling ambient air through air tunnel 44, represented in FIGS. 2 and 3 by the outwardly extending arrows numbered 45. As shown in FIGS. 2 and 3, air tunnel 44 includes a deflector 50 which extends for the length of target board 38 and causes cooling ambient air to be circulated across target board 38 for cooling test specimen(s) 46, represented in FIGS. 2 and 3 by the arrows numbered 47.

Standards 40, 42 are rotatively supported to upper ends of A-frame members 22, 24. A supporting shaft coincident with the axis of rotation in passing through standards 40, 42 rotably supports that portion of the test apparatus which tracks daily movements of the sun. In order to properly position the Fresnel-reflecting solar concentrator comprised by mirror assembly 34, 36 and reversible electric motor and related gear drive, generally designated by reference number 54, are provided for periodically rotating the mirror bed and target board assembly to track movements of the sun. The clutch preferably couples standard 40 to a shaft to rotate the mirror assembly 34, 36 and target board assembly while permitting manual positioning of the unit at any time to correct for any positioning errors.

A solar cell tracking unit 52 controls the application of electrical power to a reversible motor in order to maintain the mirror bed frame 32 perpendicular to incident rays of sunlight. A solar tracker may be of the type which includes two balanced photo cells and a shadowing device mounted above such photo cells for shading them. When an imbalance is detected resulting from one photo cell receiving more sunlight than the other photo cell, an electrical error signal is generated which is amplified and used to apply power to the drive motor 54 for rotating the unit until the photo cells are again balanced, indicating that the unit is properly positioned with respect to the sun.

Also shown in FIG. 1 is a water spray nozzle assembly, designated generally by reference numeral 51. As shown in FIG. 1, spray nozzle assembly 51 is used to periodically spray water at the test specimen(s) to simulate dew, rain, etc.

A hinge shield or cover 49 is shown coupled to the air tunnel 44 opposite the air deflector 50. A door release mechanism 47 is disposed on the air tunnel 44 for engaging and maintaining the shield in a closed position. Upon release, the shield 49 assumes the position shown in FIG. 1 such that concentrated solar radiation reflected by the plurality of mirrors 34, 36 reaches the test specimen(s) 46.

Secured to the target board 38 is a feedback device (not shown) having at least one temperature sensitive component secured in heat conductive relationship therewith. Such component may be a thermistor, thermocouple, resistance temperature device, integrated circuit temperature device or any other suitable device for detecting temperature of the feedback device. The feedback device may be formed from a standardized material having known thermal conductive properties or may be formed from a material similar to that of the test specimen(s) 46. The temperature sensitive component may be embedded within, attached to a back surface or attached to a front surface of the feedback device. Alternatively, a non-contact optical temperature sensing device may be used in order to determine the temperature of the feedback device. The feedback device is preferably coated with black paint to insure that the feedback device will absorb solar radiation impinging upon the area of the target board 38 to which the feedback device is secured. An appropriate black paint which may be used for this purpose is DUPONT DULUX Super Black High Temperature Enamel.

Referring again to FIG. 1, a controller box 57 houses the power and controller systems for the apparatus 20. A power cable 58 supplies electrical power to the apparatus 20 for powering the electric motor 54, which actuates the fan 48. A signal cable 60 is connected to the controller system disposed within the control box 57 for communication with remotely disposed devices, such as the feedback devices and input device, as will be discussed below or for communication with a central command for governing the operation of the apparatus 20 in accordance with the present invention.

Figure 4:
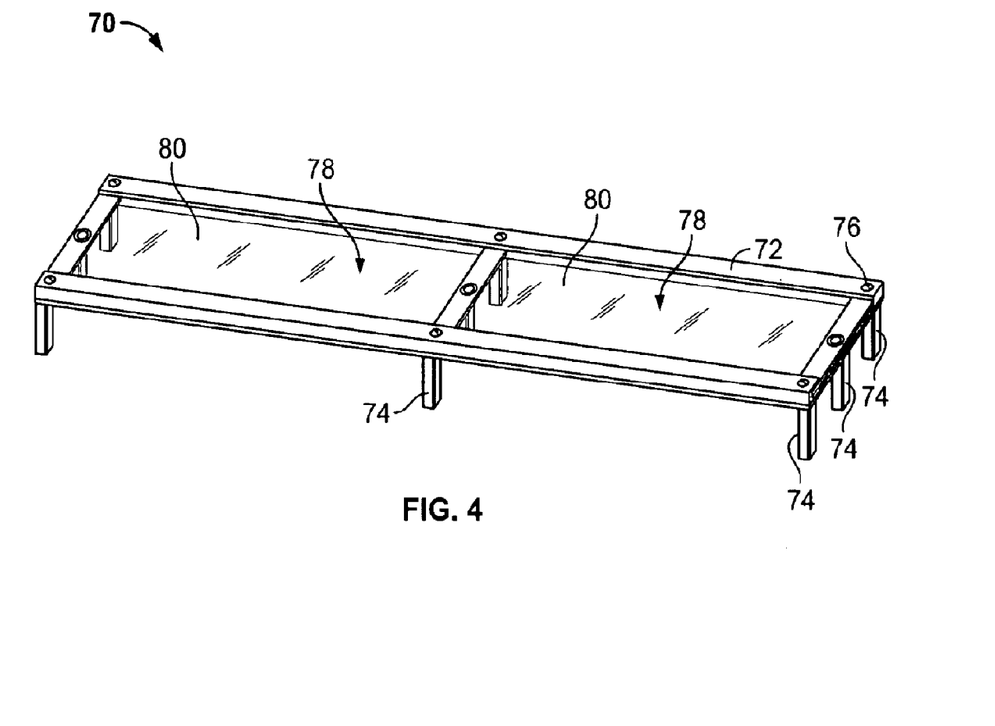
FIG. 4 illustrates a perspective view of a fixture.

Referring to FIG. 4, a temperature reduction fixture 70 for the accelerated weathering test apparatus 20 constructed in accordance with the teachings of the present disclosure is shown. The fixture 70 includes a frame 72 and a plurality of stand-offs 74. The frame 72 is generally rectangular and includes one or more openings 78. The frame 72 is spaced from the target board 38 by the plurality of stand-offs 74. Additionally, the stand-offs 74 provide the mounting of the frame 72 to the target board 38. The fixture 70 also includes a transparent element 80 that is connected to the frame in alignment with the opening 78 and to cover the opening 78.

The stand-offs 74 can be connected to the frame by methods that are known to those of ordinary skill in the art. For example, as shown in FIG. 4, each stand-off 74 can be connected to the frame 72 by a fastener 76. In another example, the stand-offs 74 and the frame 72 may be co-manufactured as a one-piece component. As shown in FIG. 4, the stand-offs 74 may be disposed anywhere along the frame. However, the stand-offs 74 can be disposed at the edges of the frame 72 so as to not block the solar rays 39 passing through the transparent element 80. To provide additional support for attaching the frame 72 to the target board 38, additional stand-offs 74 may connect the frame 72 to the target board 38. Such stand-offs 74 may be disposed along the span of the frame 72. As shown in FIG. 4, three stand-offs 74 can connect the mid-span of the frame 72 to the target board 38.

Figure 5:
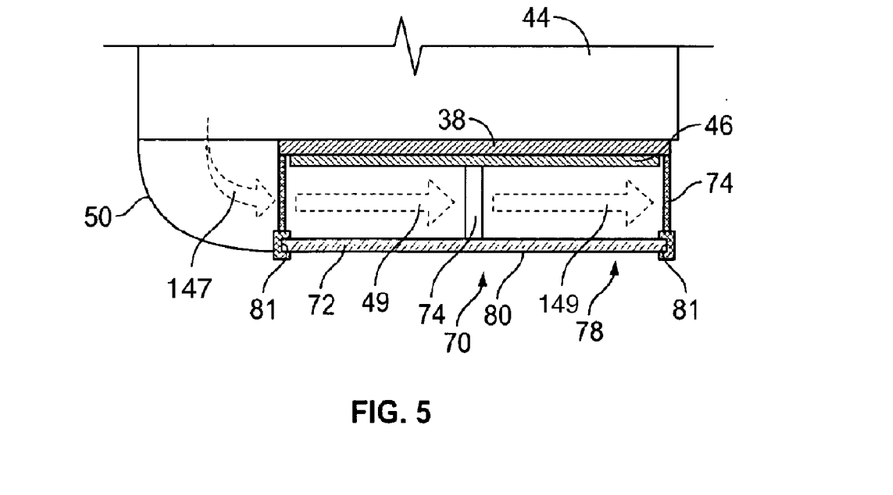
FIG. 5 illustrates a detailed sectional view of the air tunnel of FIG. 3 with the fixture of FIG. 4 operatively coupled thereto.

The frame 72 can support the transparent element 80 by methods that are known to those of ordinary skill in the art. For example, as shown in FIG. 5, the frame 72 may include a slot 81 disposed on its inner periphery to accommodate the edges of the transparent element 80. Accordingly, the thickness of this slot 81 may be slightly larger than the thickness of the transparent element 80 to securely accommodate the transparent element 80. In another example (not shown), the frame 72 may have a first frame part upon which the transparent element 80 may be placed. The frame can also include a second frame part that can then be placed on top of the transparent element 80. Accordingly, the transparent element 80 can be sandwiched between the first frame part and the second frame part of the frame 72. The second frame part can then be fastened to the first frame part to secure the transparent element 80.

Referring to FIG. 5, the frame 72 functions as an extension of the deflector 50. Accordingly, the stand-offs 74 are sized so as to provide the airflow shown by the arrows 147 from the deflector 50 into and through the fixture 70. The sides of the fixture 70 are enclosed by side walls (not shown) that may be constructed from any material so as to substantially shield the interior of the fixture 70 from the ambient air. The side walls may be constructed from wood, metal, plastic, composite materials, or combinations thereof. Alternately, the side walls may also be constructed from the a transparent material if desired.

The fixture 70 substantially shields the airflow 147 from the ambient air while permitting solar rays 39 to pass through the transparent element 80 and strike the test specimen(s) 46. Accordingly, the transparent element 80 may be chosen so as to permit ultraviolet, infrared, and invisible wave lengths of solar radiation to pass therethrough. In one embodiment of the present disclosure, the transparent panel may be formed from borosilicate glass. Additionally, the transparent element 80 may be chosen so as to filter certain wave lengths of solar radiation if desired. For example, the transparent element may partially block infrared radiation from reaching the specimen(s) 46.

As noted above, the fixture 70 functions as an extension of the deflector 50. Accordingly, the air that is shown by the arrows 47 is compressed between the frame 72 and the target board 38 to facilitate heat transfer from the test specimen(s) 46. As will be discussed in the following, the increased heat transfer provides lower operating temperatures for the specimen(s) 46 when such lower operating temperatures are desired.

Figure 6:
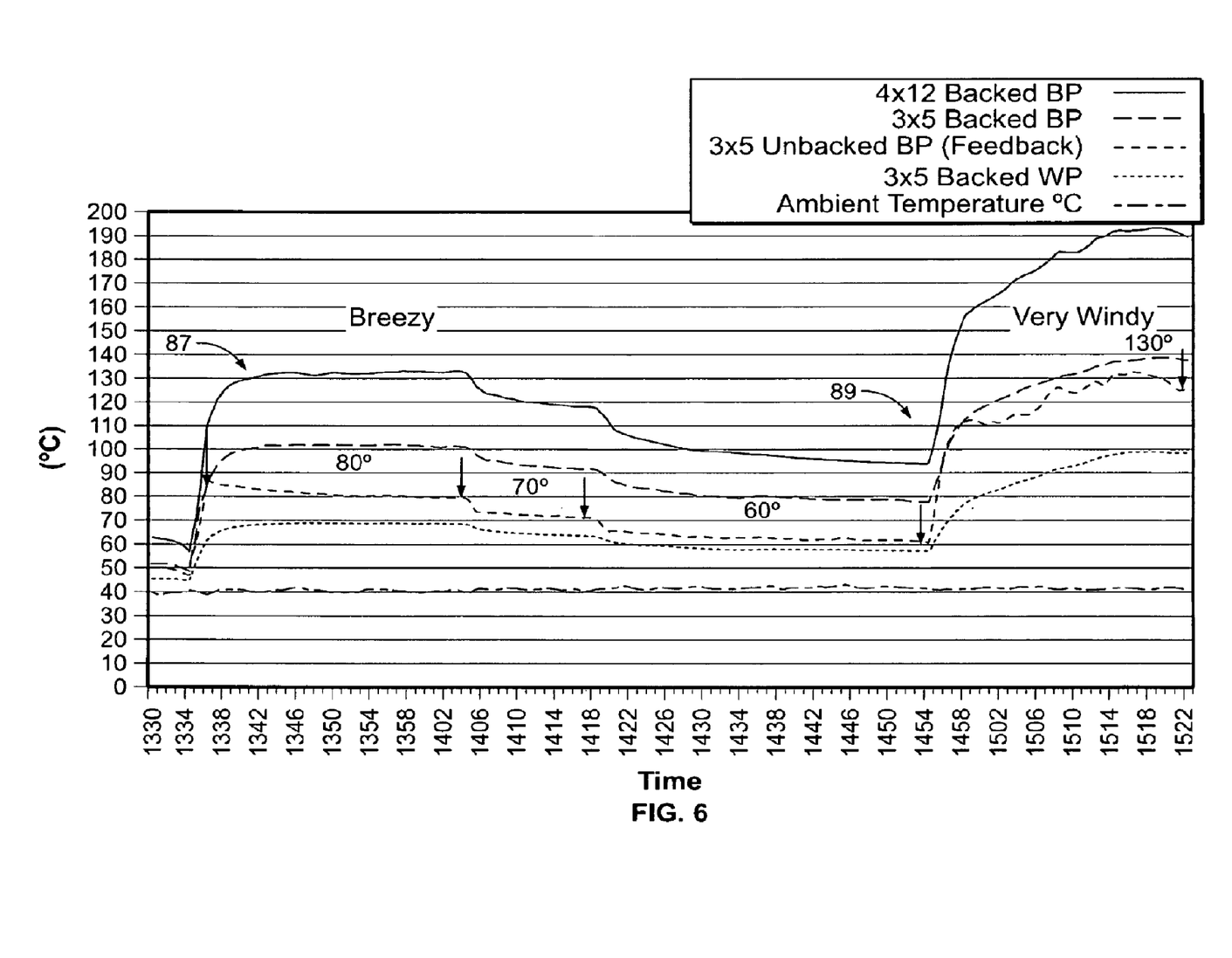
FIG. 6 illustrates a graphical representation of an operating temperature of various test specimens at different desired test specimen temperatures on the accelerated weathering test apparatus of FIG. 5 with the fixture of FIG. 4 sequentially installed and removed.

Referring to FIG. 6, temperature variations for four types of test specimen mounting configurations with the fixture 70 mounted are graphically shown where the temperature of each test specimen mounting is controlled. The temperature variations shown in FIG. 6 are for the following test specimen mounting configurations: a 4×12 (inches) backed black panel, a 3×5 backed black panel, a 3×5 unbacked black panel with control feedback, and a 3×5 backed white panel. Accordingly, the noted test specimen mounting configurations will be generally referred to herein as panels.

A test specimen 46 is typically mounted between a white panel and a black panel. The white panel can indicate the coolest temperature experienced by the specimen 46, while the black panel can indicate the hottest temperature experienced by the specimen 46. A panel may be backed or unbacked. A backed panel is a panel that has a backing, which is typically constructed of wood or metal. An unbacked panel does not have a backing. Accordingly, air can flow under an unbacked panel, thereby resulting in panel temperatures that are typically lower than a similar backed panel.

Referring to FIG. 6, the temperature of each panel is controlled in a step-down manner to achieve the desired temperature for that panel considering the ambient temperature and conditions. From a time value indicated by the arrow 87 (about 1334) to a time value indicated by the arrow 89 (about 1454), the temperature of each panel is lowered in a series of steps by setting the desired temperature and controlling the flow of compressed air 49 over each panel. At time value 89, each panel has substantially achieved its last desired temperature and the lowest possible temperature considering the ambient temperature. As shown in FIG. 6, the lowest temperature shown is about 60° C. for the 3×5 unbacked black panel with feedback and the 3×5 backed white panel. The desired temperature of each panel, after the time value 89, is reset to a higher value and simply allowed to increase. Hence the temperature of each panel is shown to rise in FIG. 6. One of ordinary skill in the art will readily appreciate that without the disclosed fixture 70, the lowest temperatures achieved for each panel as shown in FIG. 6 may not be possible considering the ambient temperature and conditions shown in FIG. 6 (i.e., breezy and windy).

Figure 7:
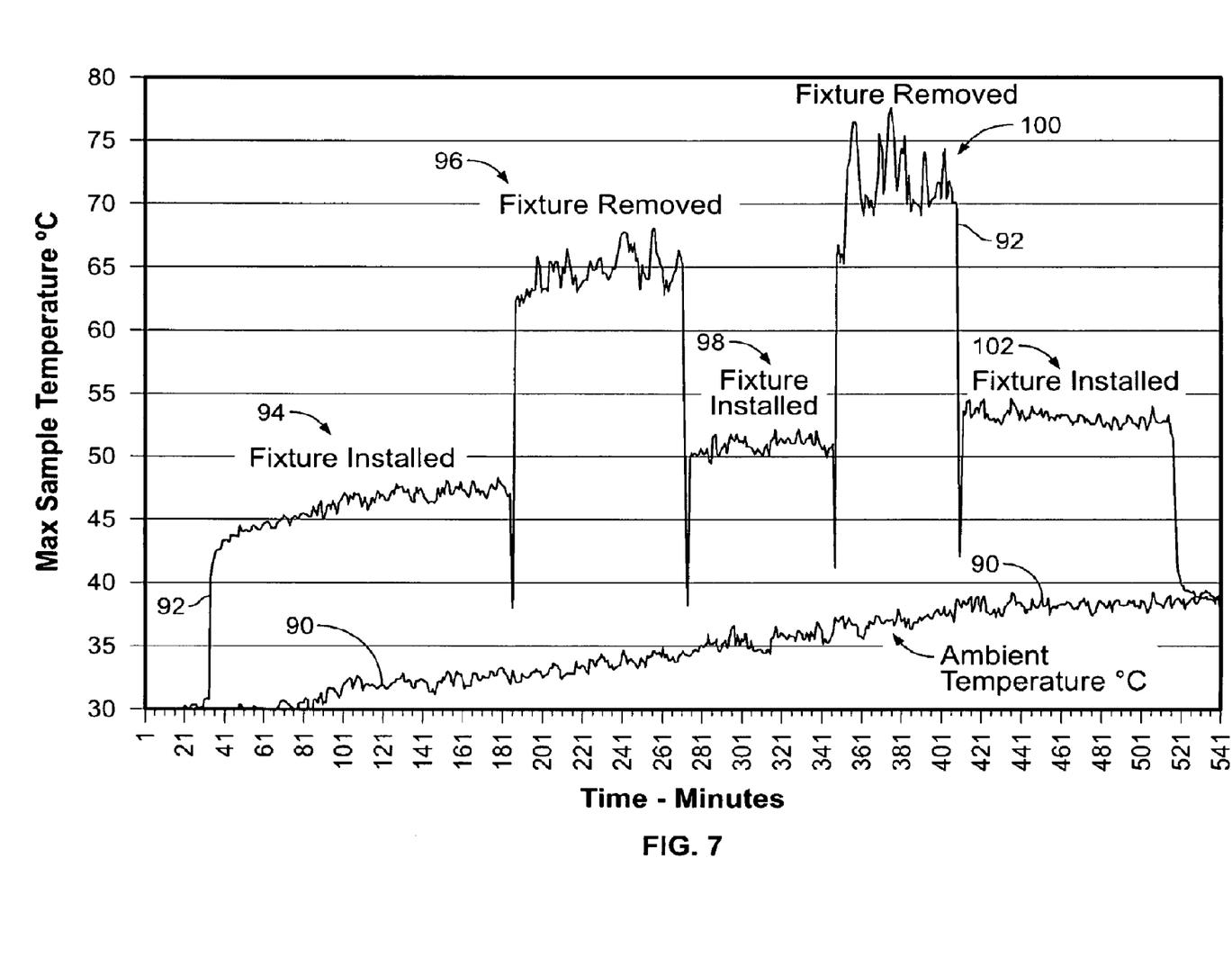
FIG. 7 illustrates a graphical representation of an operating temperature of a test specimen on the accelerated weathering test apparatus of FIG. 5 with the fixture of FIG. 4 alternately installed and removed.

Referring to FIG. 7, temperature variation plot 92 of an operating temperature of the test specimen(s) 46 with the fixture 70 being alternately installed and removed and the temperature of the test specimen(s) 46 not being controlled is graphically shown. As shown by the first time segment 94 of the temperature variation plot 92, which represents time values between about 30 to 180 minutes of exposure time, the temperature of the test specimen(s) 46 steadily climbs from about 42° C. to 47° C. In this first time segment 94, the fixture 70 is installed over the test specimen(s) 46 as the test specimen(s) 46 is exposed to the solar rays 39. The ambient temperature 90 is also shown to steadily rise during this time period.

The fixture 70 is removed at the second time segment 96 of the temperature variation plot 92, which represents time values between about 180 to 275 minutes of exposure time. As shown by the second time segment 96, the temperature of the test specimen(s) rapidly jumps to over 60° C. As described above, the increased heat transfer provided by a compressed air 149 in the fixture 70 is absent in the second time segment 96, and as a result, the temperature of the test specimen(s) 46 shows a noticeable movement from the first time segment 94.

In the third through the fifth time segments 98 to 102, respectively, the fixture 70 is removed and installed to illustrate the effects of the fixture 70 on the temperature of the test specimen(s) 46. As shown in FIG. 7, removal of the fixture 70 rapidly increases the temperature of the test specimen(s) 46. In addition to providing better heat transfer from the test specimen(s) 46, the fixture 70 substantially shields the test specimen(s) 46 from ambient wind fluctuations that may disturb the air flow 47. Accordingly, fluctuations in the temperature of the test specimen(s) 46 can be reduced.

FIG. 7 graphically illustrates the noted reduction in the temperature fluctuations of the test specimen(s) 46 when the fixture 70 is being used in the accelerated weathering test apparatus 20. Comparatively referring to the first time segment 94 and the second time segment 96 of the temperature variation plot 92, fluctuations in the temperature of the test specimen(s) 46 are more pronounced when the fixture 70 is removed. The fluctuations in the second time segment 96 are due to the disturbance of the air flow 47 over the test specimen(s) 46 by the ambient air. Such disturbances can be substantially blocked by the fixture 70 as shown in the first time segment 94. Similarly, when the fixture is removed during the fourth time segment 100, fluctuations in the temperature of the test specimen(s) 46 appear pronounced as compared to any one of the three time segments 94, 98, or 102, where the fixture 70 is being used.

As described in the foregoing, the fixture 70 allows the accelerated weathering test apparatus 20 to maintain the temperature of the test specimen(s) at a lower temperature than possible without the fixture 70. The lower temperatures of the test specimen(s) 46 are possible due to the fixture 70 providing compressed air 149 to flow over the test specimen(s) 46. Additionally, the fixture 70 reduces fluctuations in the temperature of the test specimen(s) 46 that may be caused by the ambient wind disturbing the air flow 47 from the air tunnel 44.

Furthermore, while the particular preferred embodiments have been shown and described, it will be obvious to those skilled in the art that changes and modifications may be made without departing from the teaching of the disclosure. The matter set forth in the foregoing description and accompanying drawings is offered by way of illustration only and not as limitation. The actual scope of the disclosure is intended to be defined in the following claims when viewed in their proper perspective based on the related art.

What is claimed is:

1. An accelerated weathering test apparatus of the type used to concentrate solar radiation upon test specimens including a frame supporting a reflecting solar concentrator disposed in opposition to a target board supported in an air tunnel having a deflector to circulate air across the test specimens mounted on the target board, the accelerated weathering test apparatus comprising:
    a fixture connected to the target board including a frame spaced from the target board a predetermined distance by a plurality of stand-offs, the fixture having at least one opening defined therein, and a transparent element connected to the frame in alignment with said at least one opening in a covering orientation such that the solar radiation from the reflecting solar concentrator impinges upon the test specimens,
    wherein the predetermined distance is configured such that the frame functions as an extension of the deflector and an operating temperature of the test specimens is shielded from external influences.

2. The accelerated weathering test apparatus as recited in claim 1, wherein the transparent element is substantially transparent to ultraviolet, infrared and visible wavelengths of solar radiation.

3. The accelerated weathering test apparatus as recited in claim 1, wherein the transparent element is formed from borosilicate glass.

4. The accelerated weathering test apparatus as recited in claim 1, wherein the transparent element filters certain wavelengths of solar radiation.

5. The accelerated weathering test apparatus as recited in claim 1, wherein the operating temperature is maintained in a pre-selected range of a desired test specimen temperature.

6. The accelerated weathering test apparatus as recited in claim 1, wherein the operating temperature is maintained within an offset from an ambient temperature.

7. The accelerated weathering test apparatus as recited in claim 1, wherein the frame is substantially planar.

8. The accelerated weathering test apparatus as recited in claim 1, wherein the predetermined distance is approximately at least 10 millimeters.

9. The accelerated weathering test apparatus as recited in claim 1, wherein the frame and stand-offs are formed from aluminum.

10. The accelerated weathering test apparatus as recited in claim 1, wherein the frame is configured to have a width extent and a length extent greater than a width dimension and a length dimension of the target board.

11. The accelerated weathering test apparatus as recited in claim 1, wherein the air circulated across the test specimens is compressed between the frame and the target board to facilitate increased heat transfer from the test specimens.

12. A fixture adapted for use in connection with an accelerated weathering test apparatus of the type used to concentrate solar radiation upon test specimens including a frame supporting a reflecting solar concentrator disposed in opposition to a target board supported in an air tunnel having a deflector to circulate air across the test specimens mounted on the target board, the fixture comprising:
    a frame having at least one opening defined therein and a transparent element connected to the frame in alignment with each at least one opening in a covering orientation such that the solar radiation from the reflecting solar concentrated impinges upon the test specimens; and
    a plurality of stand-offs operatively contiguous with the frame and target board to space the frame from the target board a predetermined distance that is configured such that the frame functions as an extension of the deflector and an operating temperature of the test specimens is shielded from external influences.

13. The fixture as recited in claim 12, wherein the transparent element is substantially transparent to ultraviolet, infrared and visible wavelengths of solar radiation.

14. The fixture as recited in claim 12, wherein the transparent element is formed from borosilicate glass.

15. The fixture as recited in claim 12, wherein the transparent element filters out certain wavelengths of solar radiation.

16. The accelerated weathering test apparatus as recited in claim 1, wherein the operating temperature is maintained in a pre-selected range a desired test specimen temperature.

17. The accelerated weathering test apparatus as recited in claim 1, wherein the operating temperature is maintained within an offset from an ambient temperature.

18. The fixture as recited in claim 12, wherein the frame is configured to have a width extent and a length extent greater than a width dimension and a length dimension of the target board.

19. The fixture as recited in claim 12, wherein the air circulated across the test specimens is compressed between the frame and the target board to facilitate increased heat transfer from the test specimens.

20. An accelerated weathering test apparatus of the type used to concentrate solar radiation upon test specimens including a frame supporting a reflecting solar concentrator disposed in opposition to a target board supported in an air tunnel having a deflector to circulate air across the test specimens mounted on the target board, the accelerated weathering test apparatus comprising:
    a fixture connected to the target board including a substantially planar frame spaced from the target board a predetermined distance by a plurality of stand-offs and having a plurality of openings defined therein that are in registration with the test specimens and a plurality of transparent elements formed from an ultraviolet transmissive material connected to the frame, each transparent element in alignment with one of the openings such that the solar radiation from the reflecting solar concentrator impinges upon the test specimens;
    wherein the predetermined distance is configured such that the frame functions as an extension of the deflector so that the air circulated across the test specimens is compressed between the frame and target board to facilitate increased heat transfer from the test specimens and an operating temperature of the test specimens is maintained in a narrow range close to a desired test specimen temperature, shielded from external influences.

21. An accelerated weathering test apparatus of the type used to concentrate solar radiation upon test specimens at a first temperature including a frame supporting a reflecting solar concentrator disposed in opposition to a target board supported in an air tunnel having a deflector to circulate air across the test specimens mounted on the target board, the accelerated weathering test apparatus comprising:

a fixture connected to the target board including a frame spaced from the target board a predetermined distance by a plurality of stand-offs, the fixture having at least one opening defined therein, and a transparent element connected to the frame in alignment with said at least one opening in a covering orientation such that the solar radiation from the reflecting solar concentrator impinges upon the test specimens, wherein the predetermined distance is configured such that the frame functions as an extension of the deflector and an operating temperature of the test specimens is less than the first temperature and is shielded from external influences.

22. The accelerated weathering test apparatus as recited in claim 21, wherein the transparent element is substantially transparent to ultraviolet, infrared and visible wavelengths of solar radiation.

23. The accelerated weathering test apparatus as recited in claim 21, wherein the transparent element is formed from borosilicate glass.

24. The accelerated weathering test apparatus as recited in claim 21, wherein the transparent element filters certain wavelengths of solar radiation.

25. The accelerated weathering test apparatus as recited in claim 21, wherein the operating temperature is maintained in a pre-selected range of a desired test specimen temperature.

26. The accelerated weathering test apparatus as recited in claim 21, wherein the operating temperature is maintained within an offset from an ambient temperature.

27. The accelerated weathering test apparatus as recited in claim 21, wherein the operating temperature is maintained within an offset from the first temperature.

28. The accelerated weathering test apparatus as recited in claim 21, wherein the frame is substantially planar.

29. The accelerated weathering test apparatus as recited in claim 21, wherein the predetermined distance is approximately at least 10 millimeters.

30. The accelerated weathering test apparatus as recited in claim 21, wherein the frame is configured to have a width extent and a length extent greater than a width dimension and a length dimension of the target board.

31. The accelerated weathering test apparatus as recited in claim 21, wherein the air circulated across the test specimens is compressed between the frame and the target board to facilitate increased heat transfer from the test specimens.

* * * * *